United States Patent [19]
Moran

[11] Patent Number: 5,919,361
[45] Date of Patent: Jul. 6, 1999

[54] SPRING-LOADED HYDRAULICALLY ACTIVE LIQUID CHROMATOGRAPHY COLUMN

[75] Inventor: Michael G. Moran, Crystal Lake, Ill.

[73] Assignee: UOP LLC, Des Plaines, Ill.

[21] Appl. No.: 08/992,055

[22] Filed: Dec. 17, 1997

[51] Int. Cl.[6] .................................................. B01D 15/08
[52] U.S. Cl. ...................................... 210/198.2; 210/656
[58] Field of Search .................................... 210/656, 659, 210/198.2; 96/101

[56] References Cited

U.S. PATENT DOCUMENTS

| | | | |
|---|---|---|---|
| 3,706,812 | 12/1972 | DeRosset et al. | 260/674 SA |
| 4,675,105 | 6/1987 | Martin | 210/198.2 |
| 4,769,141 | 9/1988 | Couillard | 210/198.2 |
| 5,013,433 | 5/1991 | Shalon | 210/198.2 |
| 5,158,676 | 10/1992 | Kreher | 210/198.2 |
| 5,169,522 | 12/1992 | Shalon et al. | 210/198.2 |
| 5,565,104 | 10/1996 | Priegnitz | 210/659 |
| 5,635,072 | 6/1997 | Moran | 210/659 |

OTHER PUBLICATIONS

"Optical resolution by simulated moving–bed adsorption technology," *Journal of Chromatography*, 590 (1992) pp. 113–117.

"A spring–loaded preparative HPLC column," *American Laboratory*, Sep. 1997, pp. 1–4.

*Primary Examiner*—Ernest G. Therkorn
*Attorney, Agent, or Firm*—Thomas K. McBride; John F. Spears, Jr.

[57] ABSTRACT

The adsorbent bed (25) retained in an HPLC column (1) is maintained in a constant state of compression by a spring loaded hydraulically active second column (13). A relatively small spring (14) loaded piston (15) in the second column maintains a constant hydraulic pressure in the hydraulic chamber (3) of the larger diameter HPLC column (1). Multiple small diameter columns (13) can be employed if necessary.

6 Claims, 2 Drawing Sheets

SPRING-LOADED HYDRAULICALLY ACTIVE LIQUID CHROMATOGRAPHY COLUMN

FIELD OF THE INVENTION

The invention relates to a chromatographic apparatus for use in the small to medium scale separations of chemicals such as chiral pharmaceuticals. The invention more specifically relates to a novel design for a high pressure liquid chromatography (HPLC) column including a spring loaded chamber which automatically adjusts the hydraulic pressure applied to a bed of adsorbent located in the column.

RELATED ART

U.S. Pat. No. 3,706,812 issued to A. J. De Rosset and R. W. Neuzil describes a pilot plant scale simulated moving bed adsorptive separation process unit. U.S. Pat. No. 5,565,104 to J. W. Priegnitz and 5,635,072 to M. G. Moran illustrate other valving arrangements for small scale simulated moving bed adsorptive separation units.

The separation of racemic mixtures of chiral material by continuous simulated moving bed adsorptive separation was described in a presentation conducted at PREP '91 in Arlington, Va., USA on May 13–15, 1991 and printed in the *Journal of Chromatography*, 590 (1992) pages 113–117. The article gives a diagram of a small scale system with eight adsorbent chambers and four rotary valves.

U.S. Pat. No. 5,013,433 issued to Y. Shalon describes a chromatographic column which is characterized as having a zero void volume. The invention centers upon the construction of the distribution and collection devices located at the ends of the column for assuring uniform flow of the liquid through the column.

U.S. Pat. No. 5,169,522 issued to Y. Shalon et al. describes an hydraulically active liquid chromatography column suitable for use in HPLC systems. A cylindrical bed of adsorbent is retained within an adsorbent chamber and is compressed by a piston driven by a hydraulic fluid in the hydraulic chamber. An opening is provided in the end plate of the apparatus for enabling the monitoring, maintaining and releasing of the pressure in the column as necessary. This opening may be equipped with a gauge and valve.

FIG. 2 of an article by Yehuda Shalon printed in the magazine *American Laboratory* in September 1997 illustrates a spring-loaded HPLC column. The piston applying pressure to the cylindrical bed of adsorbent may be driven downward through a threaded screw at an upper end of the column. A compressed spring intermediate the piston and the threaded screw acts directly on the piston. The spring maintains a relatively constant pressure upon the bed of adsorbent.

BRIEF SUMMARY OF THE INVENTION

The invention is a spring-loaded hydraulically active column apparatus for performing high pressure liquid chromatographic separations of mixtures of chemicals. The invention provides an intermediate size adsorption column which retains a fixed bed of adsorbent in a highly compressed and well-packed mode despite significant changes in the operating pressure of the column.

One broad embodiment of the invention may be characterized as an apparatus for performing an adsorptive separation comprising a sealed first column having a cylindrical internal volume and closed first and second ends; a bed of adsorbent located within an adsorbent chamber located within the first column, with the bed of adsorbent being compressed by a movable piston located in the internal volume of the first column and driven by hydraulic pressure maintained in a first hydraulic chamber located in the internal volume of the first column between the piston and the first end of the first column; process fluid transfer lines for delivering and removing a process fluid, which transfer lines are connected to opposite ends of the adsorbent chamber; a sealed second column having first and second ends, with a second movable piston being located within the second column and a spring being located within the second column between the first end and the second movable piston, with the spring arranged to force the second piston toward a second hydraulic chamber which is located between the piston and the second end of the second column; and, a hydraulic fluid transfer connection between the first and second hydraulic chambers.

DETAILED DESCRIPTION AND PREFERRED EMBODIMENTS

Figure 1:
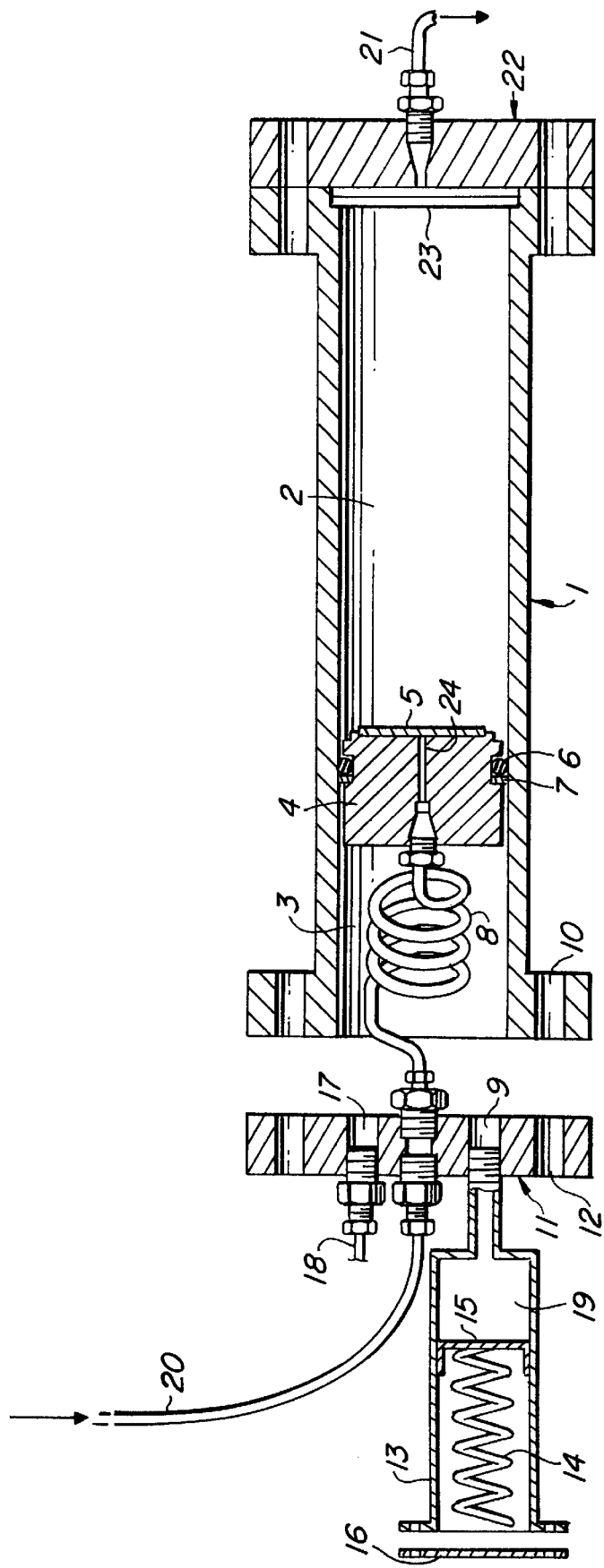
FIG. 1 is a simplified diagram of a dual column apparatus built according to the subject invention and comprising a hydraulically-loaded main adsorbent or process column 1 and a spring-loaded secondary column 13.

Simulated moving bed adsorptive separation is used commercially in a number of industries to perform useful separations of a variety of chemicals including petrochemical intermediates. It is established as a leading industrial process for the large scale recovery of para xylene suitable for the manufacture of polyesters. It is also a leading process for the recovery of normal paraffins used in the production of linear olefins which are then consumed as detergent precursors. Adsorptive separation is also being employed as a tool in the separations of a wide variety of other chemicals including chiral compounds and intermediates used in the production of experimental and therapeutic drugs. These efforts are normally conducted in small to intermediate scale pilot plants which do not require much feed stock, adsorbent or plant space. This is especially true when the materials which are to be separated are expensive due to their rarity or complicated production techniques.

In the simulated moving bed technique, the normal chromatographic profiles which develop as a multi-component feed mixture passes through a lengthy bed of adsorbent are in effect frozen within the apparatus by the periodic advancement in the location of the addition and withdrawal points of the feed, desorbent, extract and raffinate streams. A shift of the feed and withdrawal points in the direction of fluid flow simulates movement of solids in the opposite direction. Careful control of flow rates and transfer point changes allows an effective stationary phase-mobile phase pair to provide a continuous high-purity product stream. Liquid flow direction defines the "downstream" direction in the apparatus of the invention and establishes a reference point for use in the following description. The primary process streams are the feed stream, desorbent (mobile phase) stream, raffinate stream and extract stream. An optional extract recycle stream is also considered a primary process stream if present in the process.

Although the general theory and operation of a simulated countercurrent moving bed (SMB) unit does not change as its design feed rate of a unit is decreased, pilot plant scale through intermediate scale simulated moving bed adsorptive separation units have unique problems compared to large scale industrial scale plants used for petrochemical production. Many of these problems are related to the higher level of product purity required for pharmaceuticals, the higher pressures used in HPLC and other factors specific to a separation rather than the overall SMB process. For instance, SMB pilot plants have been troubled by the need to achieve the very high levels of separation between chiral compounds which have different pharmaceutical effects. These purity levels often exceed those required in large petrochemical plants.

One specific problem in processes employing SMB technology to perform HPLC separations relates to maintaining the beds of adsorbent in a well-packed immobile state. This problem arises in these processes because the inlet pressure to a particular column has a relatively wide variation in pressure. For instance, in a liquid-phase SMB unit employing several adsorbent chambers each containing a highly compacted bed of small diameter particles, the inlet pressures to a chamber may vary by 1,000 psig or more during the course of an SMB cycle. This change in pressure can compact the bed or flex internal structures of the chamber. While this movement may be exceedingly small it can lead to abrasion or grinding of the adsorbent particles. This in turn can degrade the performance of the adsorbent or form smaller particles which tend to plug the bed and further increase the pressure drop.

Difficulties also arise in performing an HPLC separation using SMB techniques due to the very small particle size (approx. 10–20 microns) of the currently available chiral stationary phases. This small size results in a very high pressure drop through the adsorbent bed. The small size particles are also more subject to channeling, which disrupts the desired composition profiles in the flowing process fluid and lowers the performance of the system. Compressing and packing of the adsorbent bed is intended in part to minimize this tendency toward channeling.

The traditional small diameter metal tubes used as adsorbent chambers in high pressure liquid chromatography (HPLC) have internal diameters up to about two cm. The traditional silica supported HPLC adsorbents can be loaded and then packed to a very high pressure in these small diameter cylinders. For example the applied pressure may reach 30,000 psi during the packing operation. This results in a very compacted almost solid bed of adsorbent which may be simply sealed off and used. However, as the desired capacity of the process unit increases it is necessary to increase the cross sectional area of the adsorbent chambers to accommodate more adsorbent. At a certain point it becomes impractical to load and compress the adsorbent in the same manner as in these small diameter chambers. The art has therefore developed alternative means to insure the integrity of the adsorbent bed. These have included the hydraulically active column described above.

During a SMB process the location at which the feed stream and the desorbent stream enters the overall process is slowing changed in a stepwise manner. All of the adsorbent chambers are linked together serially in a continuous flow path and the feed and desorbent streams push the liquid contents of several chambers through the apparatus. The pressure at the inlet of an adsorbent chamber which is receiving the feed stream therefore has to be equal to the desired outlet pressure for the raffinate stream removed from the process plus the total pressure drop across all of the intervening adsorbent chambers. As an SMB unit may contain from six to about 24 chambers the feed stream may be required to transverse from two to about ten adsorbent chambers. Therefore the pressure at the point the feed stream enters the process may be extremely high e.g. 3,000 psi. As the SMB cycle progresses the location at which the feed point enters the overall apparatus changes and the required pressure at the inlet of the chamber changes in a stepwise fashion down to a low pressure equal to that needed to push liquid through only one chamber. The greatest stepwise change in pressure occurs when a chamber switches from raffinate outflow to desorbent inflow. It is this constant repetitive change in pressure which can lead to movement. Hence the column is "dynamically active". The movement can be damaging to an adsorbent despite even the rugged characteristics of silica particles.

In some instances it is desirable to use a polymeric, e.g., resin-based adsorbent particle. This situation leads to a preference for minimizing the total pressure applied to the adsorbent particles by the process and the means employed to maintain the adsorbent bed in a compact state. The applied hydraulic pressure should only slightly exceed the process pressure. The self-adjusting nature of a spring is well suited to this situation.

Hydraulically active columns apply pressure sufficient to axially compress the adsorbent bed. However, the applied pressure is not regulated in a manner which adjusts for the changing pressures imposed during an SMB cycle. To overcome this problem the art has developed the use of spring loaded columns in which a compressed spring is used to apply a pressure to the adsorbent bed. As the spring can expand and contract, the bed can also expand and contract somewhat due to pressure changes. However, spring loaded columns are limited by the practical size of the spring which can be used. When it is desired to scale up the separation process to an intermediate scale in which the adsorbent chamber has a diameter of 25 cm or more the total force on the piston used to compress the cylindrical bed of adsorbent can be very large and it is impractical to employ a spring. For instance the pressure on a 75 cm diameter piston having an operational pressure of 1,500 psig is about 1,000,000 lbs$_f$. Simply put the required spring size is impractical for an HPLC column.

It is a primary objective of the invention to provide an apparatus for performing HPLC separations using simulated countercurrent flow moving bed methods. It is a further objective of the invention to provide HPLC adsorbent columns which are adaptable to a highly variable inlet pressure.

The subject invention achieves these objectives by the use of one or more small diameter spring loaded hydraulic chambers to apply an adjustable pressure to a larger hydraulically active chamber which compresses the adsorbent bed.

The invention may be characterized as a high pressure chromatography apparatus suitable for use in a separation process in which the apparatus is exposed to varying pressures, which apparatus comprises a dynamically axially compressed chromatography column comprising a first hydraulic chamber and an adsorbent chamber containing a bed of solid particulate adsorbent; at least one spring loaded second hydraulic chamber of smaller diameter than the first hydraulic chamber; and, a fluid transfer conduit connecting the first and second hydraulic chambers.

The overall structure and operation of the subject invention can be best described by reference to the Drawing. The Drawing shows a simplified diagram of a single adsorption chamber. The number of adsorbent chambers used in a simulated moving bed process may vary between different configurations to suit the situation. Most embodiments of such processes will have eight or more chambers, with twenty-four being about the maximum practical number of chambers. This description and the figures are premised on the adsorbent chambers used in the process each containing a single bed of adsorbent. This is not a requirement as the adsorbent can be distributed between several beds within a single chamber. While this description of the figures was presented on the basis of all the flows through the adsorbent beds being in a downward direction, there is no inherent requirement for this to be so.

Referring now to FIG. 1, the largest component of the apparatus is the primary cylinder or column 1 which functions as a hydraulically-loaded (compressed) chromatography column. During use and operation the primary column 1 is sealed at its upper end by a top flange 11 and at its lower end by a lower flange 22. This forms a cylindrical internal volume which is divided into two chambers by a movable first piston 4. One or more O-rings 6 and/or seal rings 7 can be present on the piston to help prevent passage of either fluid in the column around the piston 4. The volume below the piston in this view, with this direction being relative to the normal flow of liquid in the column, comprises a cylindrical adsorbent chamber 2. During operation the chamber 2 is filled with a densely packed bed of solid particulate adsorbent. The remainder of the internal volume of the primary column 1 is comprised of the hydraulic chamber 3. This chamber 3 fills the space between the flange 11 and the piston 4 at the upper end of the apparatus.

During operation a process stream is charged to the column through process line 20. During a complete SMB cycle, the composition and pressure of the process stream will vary greatly. The transfer lines are connected to the apparatus through fittings of customary design threaded into the flanges. The incoming process stream is thereby delivered to a flexible transfer line 8 present in the hydraulic chamber 3. The transfer line 8 is shown as coiled not to indicate that it is spring-like but rather to indicate its flexible nature which will allow the transfer line to accommodate any movement of piston 4. The piston could travel to the lower end of the primary column when for instance an adsorbent bed is being replaced with different or fresh adsorbent. At this time the lower flange 22 is removed and the piston is used to simply push the adsorbent out of the bottom of the column. However, during normal operation the piston is essentially fixed in position.

The incoming process stream of line 20 is thereby delivered by line 8 to the transfer channel 24 extending through the piston. The channel delivers the liquid to the fluid distribution frit 5 on the face of the piston. A liquid distribution means not shown may be located between the face of the piston and the frit for purposes of ensuring uniform distribution of the incoming liquid across the upper surface of the adsorbent bed. This is important as it is desired to maintain plugflow conditions across the cross section of the adsorbent bed. At the outlet end of the adsorbent chamber, a related problem occurs in that there should be uniform collection of the liquid across the entire cross section of the adsorbent bed. There is therefore provided a liquid collection and frit means 23 having a number of channels or other open volumes which allow free flow of the liquid to a central conduit leading out of the chamber. The process stream then flows through a port in the outlet flange 22 through a threaded fitting and into the outlet transfer line 21. The transfer line 21 and the transfer line 20 may be connected to valves regulating the flow of the process liquid or directly to the next downstream adsorbent chamber or directly to storage tanks for the feed and product streams.

The upper flange 11 has three ports for liquid transfer plus numerous openings 12 spaced around the periphery of the flange. The openings 12 are aligned with the openings 10 in the body of the primary chamber 1 to allow the flanges to be bolted to the primary chamber. A similar arrangement is provided to attach the lower flange. Flexible sealing means such as a gasket or O-ring can be employed at one or both ends of the apparatus to enhance the seal. The hydraulic fluid transfer port 17 is used for inserting the hydraulic fluid into the hydraulic chamber 3, for allowing the escape of air or other gases previously present in the chamber and for increasing the pressure of the hydraulic fluid up to the expected operating pressure. This port may also be used for the removal of the hydraulic fluid. The port is connected through threaded fittings to a hydraulic fluid transfer line 18 which may lead to the appropriate valves and other apparatus for this filling and fluid pressurization step. Although the port is shown in the drawing as being located in the upper flange 11, it could be located in the sidewall of the chamber if desired. Alternatively, two or more hydraulic fluid transfer ports can be located at the upper end of the chamber to allow more convenient removal of liquid and gases from the hydraulic chamber.

The third fluid transfer port 9 in the inlet flange 11 is directly connected via a screw-on coupling to a smaller second column 13. The secondary column 13 is preferably also cylindrical but has a much smaller diameter and cross-sectional area than the primary column 1. A flange 16 is shown as closing only the left-hand end of the column 13 but flanges could be used at both ends of the column if desired. The secondary column 13 differs from the primary column 2 in that it does not contain any adsorbent. Instead the secondary column has a hydraulic chamber 19 which is filled with the same hydraulic fluid as the hydraulic chamber 3 of the primary column 1. The open fluid communication between these two hydraulic chambers through the port 9 causes essentially instantaneous equalization of the pressures in the two chambers. The secondary column 13 has a spring 14 which drives a piston 15 against the hydraulic chamber of the secondary column. By proper choice of the size and strength of the spring 14, any change in the operating pressure in the adsorbent chamber of the primary column can be easily compensated for. Any settling or other disturbance of the adsorbent bed in the adsorbent chamber 2 of the primary column will result in a corresponding movement of the piston 4 in the primary column. However, this movement will not reduce the pressure in the hydraulic cylinder 3 and thus will not reduce the pressure applied onto the adsorbent bed because of the action of the spring 14 against the secondary hydraulic chamber 19.

Figure 2:
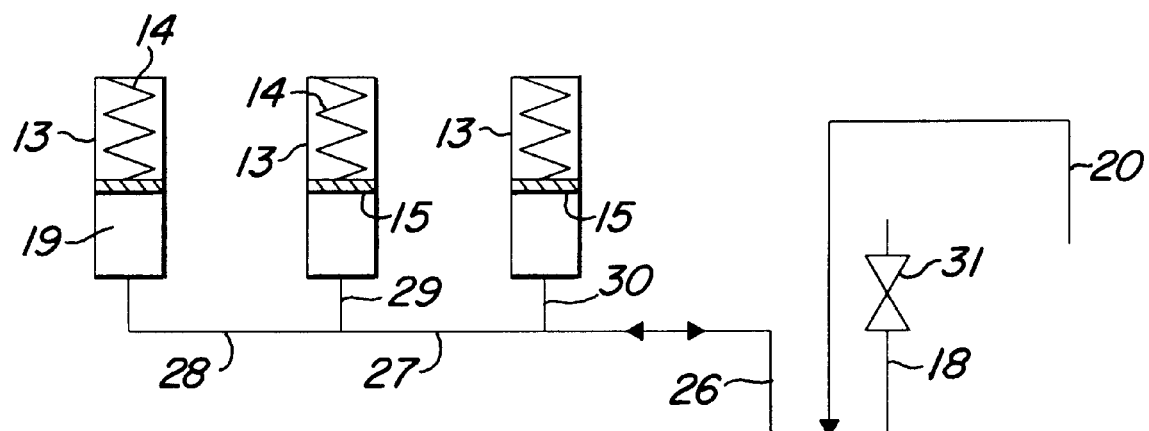
FIG. 2 illustrates a large primary column 1 interconnected with three spring-loaded secondary columns 13.
Figure 2:
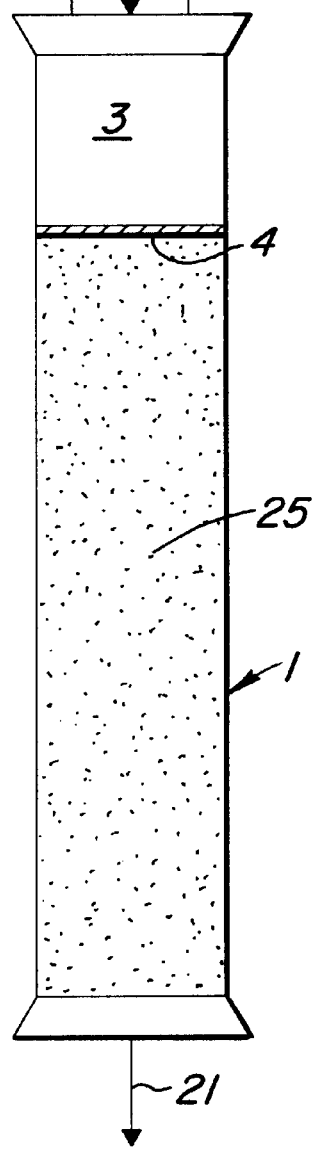

FIG. 2 illustrates the use of a plurality of secondary columns 13 to maintain a desired pressure in a primary hydraulic chamber 3 of a much larger adsorption column 1. For instance, if this drawing was to scale and each of the smaller secondary columns 13 is approximately 5 centimeters in diameter then the larger adsorption column 1 would be about 20 centimeters in diameter. A plurality of smaller columns may be desired when a very high ratio in column cross section exists. Movement of the large piston a short distance may require the delivery or removal of a large percentage of the volume of a single small column. The ratio in piston diameters and corresponding cross-sectional area of the two columns can be much higher than this. A ratio of ten to one or more in piston diameters is possible. The total force imposed upon the larger piston 4 by the pressurized fluid can therefore be extremely high due to the large surface area of the piston. Attempting to compensate for changes in such a large load through the use of a single or even multiple springs attached to the piston 4, would result in the need for excessively large and powerful springs. Instead the invention employs the hydraulic force supplied by the three smaller secondary chambers 13 each having a spring 14 which pushes upon a small piston 15. This drives hydraulic fluid from the chamber 19 through the connecting lines 26, 27, 28, 29 and 30 into the hydraulic chamber 3 of the primary column of the apparatus. The hydraulic fluid may also flow from the primary hydraulic chamber to the secondary chambers. As the force applied against the pistons 15 in the secondary chambers 13 is much smaller due to the smaller surface area of the pistons, much smaller and more practically sized springs 14 are sufficient. Also shown on this drawing, is a valve 31 in the fluid transfer line 18 for the hydraulic fluid to and from the hydraulic chamber 3 of the primary adsorption column 1. Another feature shown on this Figure is the adsorbent bed 25 located between the piston 4 and the outlet end of the adsorbent chamber.

Any reference to zone numbers in reference to a simulated countercurrent moving bed process are to the nomenclature which have become established in the SMB art. Zone numbers are used and illustrated in U.S. Pat. Nos. 2,985,589; 3,310,486; 3,392,113 and 4,475,954 which are incorporated herein by reference for their description of the operation of the SMB process and equipment for its performance. The process uses a plurality of serially connected adsorbent chambers, with the number of chambers in any one zone of the process depending on such factors as adsorbent performance, desorbent strength, etc. The adsorbent chambers used are serially interconnected by a circuit of conduits and valves. This interconnection forms a loop containing all of the beds, with a point or points to add and remove the primary process streams between each bed located at regular intervals along the loop. The location of various zones used in the separation process, such as the adsorption zone is moved around the loop while the adsorbent remains stationary. This advancement of the zones is accomplished by periodically opening and closing the valves by a computerized control system. This periodically advances the inlet points of each zone one chamber per step in a repeated cycle.

For purposes of discussion, assume the feed stream enters a first chamber "B" and then flows downstream into a second chamber "A". The separation which occurs while the feed stream passes through the adsorbent retained in chambers "B" and "A" results in the formation of a raffinate stream having a higher concentration, relative to the feed stream, of one or more component(s) originally present in the feed stream, components which are less strongly held by the adsorbent. Often, but not necessarily, the most strongly adsorbed component is the desired product. Adsorption of this component produces the raffinate stream comprising the less strongly held component(s) and admixed desorbent material which is withdrawn from the adsorption zone. A back-pressure valve or regulator is preferably used as the device which regulates the flow rate of the raffinate stream out of the process. The raffinate flow rate is preferably not really set by this valve. Preferably the valve's primary function is to maintain a constant pressure at this point in the system. The actual flow rate of the raffinate stream is preferably set by the flow rates of the other streams into and out of the process, with the raffinate stream equal to the difference in these flows.

The point at which the feed stream enters an adsorbent chamber marks the beginning of the adsorption zone or Zone I. Zone I continues to the point at which the remaining components of the feed stream are withdrawn as the raffinate stream. The point at which the mobile phase (desorbent) enters an adsorbent chamber marks the beginning and upstream end of the desorption zone or Zone III. Zone II is a purification zone between the point at which the extract stream is removed and the feed stream is passed into the apparatus. Zone IV separates the adsorption and desorption zone and lies between the raffinate withdrawal point and the mobile phase injection point.

As a further example of this zone nomenclature, if the apparatus comprises 16 adsorbent chambers, referred to as chambers "A" through "P", a feed stream may be charged to the inlet of adsorbent chamber "H" and passed through 6 adsorbent chambers before being removed from the apparatus at the outlet of adsorbent chamber "C" as the raffinate stream withdrawn from the apparatus. In this same example, the mobile phase or desorbent stream can be charged to the inlet of adsorbent chamber "A" with the resultant extract stream being removed from the outlet of adsorbent chamber "O". This forms the extraction zone or Zone III of the apparatus comprising 3 adsorbent beds. In this specific example, an external recycle stream could be withdrawn from the outlet of adsorbent chamber "B" located one chamber downstream from the point of removal of the raffinate.

The flow rates of the feed stream, desorbent stream and extract stream are all regulated on the basis of set flow rates, which are preferably held constant. The raffinate stream rate is on pressure control. A flow rate control valve (not shown) regulates the effluent rate of the extract stream to be less than the feed rate of the desorbent stream. The outlet rate of the raffinate stream is set by a pressure control valve also not shown. The rate of flow of the raffinate is therefore automatically equal to the two input streams minus the extract stream.

The feed and desorbent streams will normally be fed to the unit by pumps from small tanks located close to the unit. The raffinate and extract streams will normally be collected in similar tanks located close to the unit. Both the raffinate and/or extract streams may be sent to thin film evaporators, fractional distillation zones or crystallizers or other facilities to recover solvent, the intended product and other compounds. The stream containing the undesired compound may be sent to a conversion zone such as an isomerization or racemization zone to produce more of the desired product and then recycled as feed.

The adsorbent particles located in the adsorbent chamber may be in the form of any shape, e.g., sphere or extrudate, and of any size suitable for use in high pressure liquid chromatography. It is highly preferred the particles are spherical. The composition of the adsorbent is not a controlling factor in the invention, which may employ any suitable solid adsorbent. Examples of possible adsorbent material include the cross-linked organic resins, natural or synthetic zeolites including zeolites X, Y, L, ZSM, Beta and omega, silica, silica-alumina, the various adsorptive aluminas, pillared and mesoporous materials including pillared clays, and nonzeolitic molecular sieves (NZMS), such as silica alumino-phosphates and aluminophosphates, and proprietary chiral stationary phases. Chiral stationary phases are described in U.S. Pat. Nos. 5,254,258 and 5,290,440. Further information specific to the separation of chiral compounds may be obtained from U.S. Pat. No. 5,518,625 which is incorporated herein by reference.

The mobile phase or desorbent may be any compound or mixture of compounds which is effective at the chosen operating conditions, does not react with either the adsorbent or the compounds being separated and is tolerable in or totally separable from the intended products. The desorbent may contain a chiral moiety. Depending on the compounds being separated the desorbent may for example comprise water, ethanol, methanol, benzene, toluene, a dialkylbenzene or a halogenated hydrocarbon or a mixture of compounds.

The subject apparatus can be constructed from commercially available components. Suitable valves and actuators for an SMB process are available commercially. The conduits and connectors may be of standard design for pilot to intermediate scale pharmaceutical plants or HPLC instruments used for the desired separation in the relevant industry. The chambers may be made from carbon or stainless steel or other metals as dictated by mechanical and process design factors.

A preferred embodiment of the subject invention can accordingly be characterized as an apparatus for performing high pressure liquid chromatography which comprises a dynamically axially compressed chromatography column comprising a first hydraulic chamber and an adsorbent chamber containing a bed of solid particulate adsorbent; at least one spring loaded second hydraulic chamber of smaller diameter than the first hydraulic chamber; and, a fluid transfer conduit connecting the first and second hydraulic chambers.

Operating conditions which may be used in the apparatus include a temperature of about −50 to 300 degrees C., preferably 20 to about 100 degrees C. It is generally preferred that the apparatus is operated with a positive inlet pressure in the general range of about 700 to 25000 kPa. The pressure at the inlet to the chamber will vary as the process "steps" through the simulated moving cycle. Depending on operating mode, the pressure will be highest when the mobile phase or feed is being charged directly into the column as the entry point in the process. The pressure at the inlet will therefore vary during the performance of the process. A range of from 3000 psig to about 100 psig is possible.

Representative flow rates for a small scale unit are 0.1–2.0 ml/min for the feed and 2–20 ml/min for the desorbent. Such units would employ conduits having internal diameters of about 0.3 to about 0.6 cm and could produce several hundred kg/year or more of dry product depending on the ease of separation. Intermediate scale pharmaceutical units would have quite a bit larger flow rates, with the maximum feed flow rate being limited only by equipment and economic considerations. The total amount of dry product recovered from the extract in these units could reach 1000 kg/day. The subject invention finds its greatest utility in adsorbent columns having diameters greater than about 10 cm. Such columns may have diameters up to 100 cm or more. The invention can also be applied in large petrochemical plants.

As previously mentioned chromatographic separations can be applied to a wide range of chemical compounds. Rather unusual chemicals such as chiral pharmaceutical intermediates are just one example. Fermentation broths are another. Nonchiral alkyl aromatics, halogenated aromatic compounds or aromatic compounds containing hetero atoms may also be separated using the subject invention. The aromatic compounds may have from one to four or more benzene rings and two or more alkyl groups per ring structure. Compounds having a ring structure other than a benzene ring can be separated in this apparatus. Naphthalenes and indanes are suitable feeds as are oxygenated aromatics such as ethers, esters and alcohols, and carbohydrates including saccharides. Organic acids, proteins and amino acids are other classes of suitable feed compounds. The subject apparatus and process can be used for the separation of one specific compound from a mixture or for the separation of a class of compounds from one or more classes of different compounds. The recovery of normal paraffins from admixture with branched paraffins and/or aromatic hydrocarbons is an example of this type of separation.

What is claimed:

1. An apparatus for performing an adsorptive separation, said apparatus comprising:

a. a sealed first column having a cylindrical internal volume and closed first and second ends;

b. a bed of adsorbent located within an adsorbent chamber located within the first column, with the bed of adsorbent being compressed by a movable piston located in the internal volume of the first column and driven by hydraulic pressure maintained in a first hydraulic chamber located in the internal volume of the first column between the piston and the first end of the first column;

c. process fluid transfer lines for delivering and removing a process fluid, which transfer lines are connected to opposite ends of the adsorbent chamber;

d. a sealed second column having first and second ends, with a second movable piston being located within the second column and a spring being located within the second column between the first end and the second movable piston, with the spring arranged to force the second piston toward a second hydraulic chamber which is located between the piston and the second end of the second column; and, e. a hydraulic fluid transfer connection between the first and second hydraulic chambers.

2. The apparatus of claim 1 wherein the cross-sectional area of the first column is at least three times larger than the cross-sectional area of the second column.

3. A high pressure liquid chromatography apparatus suitable for use in a separation process in which the apparatus is exposed to varying pressures, which apparatus comprises:

a. a dynamically axially compressed chromatography column comprising a first hydraulic chamber and an adsorbent chamber containing a bed of solid particulate adsorbent;

b. at least one spring loaded second hydraulic chamber of smaller diameter than the first hydraulic chamber; and, c. a fluid transfer conduit connecting the first and second hydraulic chambers.

4. The apparatus of claim 3 further characterized in that the apparatus comprises at least two spring loaded hydraulic chambers of smaller diameter than the first hydraulic chamber.

5. The apparatus of claim 3 wherein the second hydraulic chamber is directly connected to one end of the dynamically axially compressed chromatography column.

6. The apparatus of claim 3 wherein the first hydraulic chamber has a cross-sectional area at least three times as large as the internal volume of the second hydraulic chamber.

* * * * *